United States Patent [19]

Paar et al.

[11] Patent Number: 5,221,701
[45] Date of Patent: Jun. 22, 1993

[54] ORGANOTIN COMPOSITIONS CONTAINING OXAZOLIDINE DISPERSION MEDIA, A PROCESS FOR THEIR PRODUCTION AND THE USE THEREOF

[75] Inventors: Willibald Paar; Helmut Hönig, both of Graz, Austria

[73] Assignee: Vianova Kunstharz, A.G., Werndorf, Austria

[21] Appl. No.: 834,158

[22] Filed: Feb. 12, 1992

[30] Foreign Application Priority Data

Feb. 12, 1991 [AT] Austria .................................. A294/91

[51] Int. Cl.$^5$ ...................... C08G 65/26; C08L 63/00; C25D 9/00
[52] U.S. Cl. .................................. 523/404; 204/181.7; 523/414; 523/415; 523/417; 525/523; 525/526; 525/528; 528/45; 528/92; 528/107
[58] Field of Search .................. 204/181.7; 523/404, 523/414, 415, 417; 525/523, 526, 528; 528/92, 45, 107

[56] References Cited

U.S. PATENT DOCUMENTS 4,683,285  7/1987  Paar et al. ........................ 528/107
4,865,704  9/1989  Saatweber et al. ................ 523/415

Primary Examiner—John C. Bleutge
Assistant Examiner—Frederick Krass
Attorney, Agent, or Firm—Breiner & Breiner

[57] ABSTRACT

The invention relates to organotin compositions, to a process for their production, and to their use in catalyzing the crosslinking reactions of cationic paint binders crosslinkable by transesterification and/or transurethanization and/or by the reaction of terminal double bonds. The organotin compositions are prepared by dispersion of dibutyltin oxide in a dispersion medium comprising at least one substituted oxazolidine compound and, if appropriate, specially chosen water-tolerant organic solvents. Cationic paints, especially cathodically depositable electrocoating paints, catalyzed by the organotin compositions have very good sedimentation stability in dilute paint batches and show no surface defects in the stoved paint films.

7 Claims, No Drawings

ORGANOTIN COMPOSITIONS CONTAINING OXAZOLIDINE DISPERSION MEDIA, A PROCESS FOR THEIR PRODUCTION AND THE USE THEREOF

FIELD OF INVENTION

The invention relates to organotin compositions, to a process for their production, and to their use in catalyzing the crosslinking reactions of cationic paint binders.

BACKGROUND OF INVENTION

Cationic paint binders which can be employed according to the present invention, especially for the formulation of cathodically depositable electrocoating paints, crosslink to a significant extent at elevated temperature by transesterification, transurethanization, or by the reaction of terminal double bonds. It is known that crosslinking reactions of this type are catalyzed by metal compounds. In the curing of cathodically deposited paint films, such a catalysis is necessary virtually in all cases in order to attain the spectrum of properties required by industrial users.

The most important catalysts presently used in industry are organic compounds of tetravalent tin which are employed, for example, as dibutyltin oxide $(C_4H_9)_2SnO$, as dibutyltin dilaurate $(C_4H_9)_2Sn(OCOC_{12}H_{25})_2$ or as reaction products of dibutyltin oxide with alcohols or phenols. However, all of these catalysts have disadvantages.

Thus, dibutyltin oxide is a solid which has to be incorporated in the paint batch in as finely divided a form as possible, since it is fully effective as a catalyst only in solution. Longer homogenization times are therefore necessary when this catalyst is employed. If the comminution is effected by grinding in a paint binder, as is frequently the custom with pigments and extenders, then the catalytic effect of the dibutyltin oxide can be set off or initiated by the temperature rise occurring in the grinding process, and the reactivity of the binder can be prematurely activated to an undesirable degree. On the other hand, the use of dispersion media which are inert toward the binders gives rise to non-crosslinked molecular segments in the stoved film and is likewise unsuccessful. When dibutyltin dilaurate is used, acid is liberated by hydrolysis which can cause interference, especially in the operation of electrocoating plants. Dibutyltin oxide and dibutyltin dilaurate are also often not fully compatible with the paint binders used. In many cases this impairs storage stability, especially that of dilute paints used as a topping-up material in electrocoating plants.

The reaction products of dibutyltin oxide (DBTO) with alcohols or phenols, as described in EP 0,261,486 B1, possess in the ready-for-use paint excellent compatibility and stability. However, at the temperatures necessary for the crosslinking of the deposited films, decomposition products form during the crosslinking process which cause surface defects in the stoved paint film, such as pinholing and cratering.

It has now been found that an industrially advantageous catalysis for the crosslinking reactions of cathodically depositable paint binders for electrocoating paints is possible even when using dibutyltin oxide, if the mechanical dispersion of the dibutyltin oxide is effected in a mixture of at least one oxazolidine compound and specific solvents.

SUMMARY OF INVENTION

Accordingly, the present invention relates to organotin preparations which are characterized in that they comprise dibutyltin oxide, present in a particle size of from 0.1 to 5 μm after mechanical dispersion, and a dispersion medium which consists of (a) 60 to 100% by weight of at least one substituted oxazolidine compound, partially or fully protonized as appropriate, which is obtained by reacting a hydroxyalkylamino compound with formaldehyde, contains at least one oxazolidine structural element and has a hydroxyl value, based on primary hydroxyl groups, of up to 50 mg KOH/g and a (calculated) molecular weight of 500 to 4000, (b) 0 to 40% by weight of at least one water-tolerant solvent which is compatible with the component (a), is non-reactive toward dibutyltin oxide and has a boiling point between 150° and 250° C., optionally in conjunction with up to 20% by weight, based on the amount of component (b) of a surfactant, and (c) 0 to 40% by weight of at least one water-tolerant solvent having a boiling point between 100° and 150° C., the percentages of components (a), (b) and (c) totalling 100, and the organotin preparations having a dibutyltin oxide content (based on the tin content) of 5 to 30% by weight, and preferably of 12 to 25% by weight.

The invention further relates to a process for the production of the organotin preparations, to the use thereof in catalyzing the crosslinking reactions of cationic paint binders for cathodically depositable electrocoating paints, crosslinkable by transesterification and/or transurethanization and/or by the reaction of terminal double bonds, and to cationic paints, especially to cathodically depositable electrocoating paints, catalyzed by the organotin preparations according to the invention.

An oxazolidine structural element according to this invention is the unit

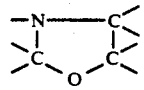

Substituted oxazolidine compounds, as obtained by the reaction of hydroxyalkylamino compounds with formaldehyde contain this unit and are used as component (a) of the dispersion medium. Examples of such products which have one or more oxazolidine structural elements and a (calculated) molecular weight of 500 to 4000 are described in Austrian Patent No. 380,264, corresponding to U.S. Pat. No. 4,683,285, and Austrian Patent No. 380,266. In order to prevent the occurrence of a reaction of the oxazolidine compounds with the dibutyltin oxide at the elevated temperature prevailing in the dispersion process, these compounds should contain only minor quantities of primary hydroxyl groups. A hydroxyl value of 50 mg KOH/g must not be exceeded. Any protonizable groups of these compounds can be completely or partially neutralized before or after the dispersion process.

High-boiling solvents which have a boiling point between 150° and 250° C., are compatible with component (a), are non-reactive toward dibutyltin oxide and possess adequate water tolerance, are employed as component (b). Water tolerance becomes important when the organotin preparation (including component (c)) is introduced in the selected water-borne paint binder without any phase separation taking place. Solvents of this type used to advantage are dialkyl ethers of dialkylene and trialkylene glycols or 2,2,4-trimethylpentanediol monoisobutyrate, sold under the brand name Texanol.

Up to 20% by weight (based on component (b)) of the above solvents of component (b) can be replaced by surfactants. These are essentially alkoxylated phenols or acetylene derivatives of the type 2,4,7,9-tetramethyl-dec-5-in-4,7-diol. The solvents of component (c) are water tolerant solvents having a boiling point between 100° and 150° C. The primary purpose of these solvents, such as ketones or alkyl ethers of ethylene glycol and propylene glycol, is to adjust the viscosity of the organotin compositions to a level which is advantageous for their handling. The dispersion of commercial dibutyltin oxide in the appropriate medium is performed using traditional grinding devices such as bead mills or triple-roll mills. The target particle size should be below 5 μm, which ensures that the dibutyltin oxide present in solution is catalytically effective, account being taken of the homogenization times normally used in the production of cathodically depositable electrocoating paints.

The organotin compositions which have a dibutyltin oxide content of 5 to 30% by weight, preferably of 12 to 25% by weight, (based on the tin content), can be added in concentrated form to the binder, to a pigment grinding resin that may be used or to the pigment paste, protonization being carried out in conjunction with the binder, if appropriate. However, provided that the preparations contain protonizable groups, they may also be added during the operation of an electrocoating plant to the dilute paint or to the bath material in neutralized form and after treatment with water and/or auxiliary solvents.

The catalyzed electrocoating paints contain 0.1 to 3.0% by weight, preferably 1.0 to 2.0% by weight, calculated on the binder solids, of tin in the form of the organotin compositions.

The organotin compositions are also perfectly compatible with the paint binders at low temperatures. Because of the organophilic nature of the dispersion medium, the dibutyltin oxide remains in the resin phase of the dilute paint and hence also in the film, largely freed from water by the endosmosis taking place during the electrocoating process.

The paint binders whose crosslinking reaction via transesterification, transurethanization or the reaction of terminal double bonds can be catalyzed by the organotin preparations according to the invention are known in the art. Further details regarding the synthesis and chemistry of these products are therefore known to one skilled in the art.

PRESENTLY PREFERRED EMBODIMENTS

The examples below elucidate the invention without limiting its scope. All parts and percentages are by weight unless stated otherwise.

(A) Preparation of the Dispersion Medium (A1) An oxazolidine compound is prepared by reacting 380 parts of a bisphenol A diglycidyl ether (epoxide equivalent weight about 190) with 268 parts (1 mole) of tallow fatty amine and 104 parts (0.8 mole) of diethylaminopropylamine, followed by reaction with 66 parts (2 moles) of 91% paraformaldehyde, 42 parts of water of reaction being separated off in vacuo. 100 parts of the reaction product are mixed with 30 parts of Texanol, 5 parts of a 50% by weight solution of an acetylene-based surfactant (2,4,7,9-tetra-methyl-dec-5-in-4,7-diol) in 2-ethylhexanol and 11.6 parts of monoethylene glycol monobutyl ether. The hydroxyl value of the primary hydroxyl groups is zero, the molecular weight is about 780, and the solids content is 70%.

(A2) A dioxazolidine is formed from an adduct, obtained from 116 parts (1 mole) of hexamethylenediamine and 500 parts (2 moles) of an industrial mixture of glycidyl esters of 1,1-dimethyl-($C_7$-$C_9$)-alkanecarboxylic acids, and 66 parts (2 moles) of 91% paraformaldehyde, 42 parts of water of reaction being separated off azeotropically. The petroleum ether (boiling range 80° to 120° C.) used as entraining agent is removed in vacuo when the theoretical amount of water has formed. 100 parts of the reaction product are mixed with 20 parts of Texanol. The hydroxyl value of the primary hydroxyl groups is zero, the molecular weight is about 640, and the solids content is 83%.

(A3) 100 parts of the dioxazolidine compound prepared in (A1) are mixed with 30 parts of diethylene glycol dimethyl ether and 4 parts of an ethoxylated nonylphenol having a molecular weight of about 340 (brand name Triton X35). The solids content is about 75%.

(A4) One mole of a disecondary amine is prepared at 80° C. from 640 parts of a polypropylene glycol-based epoxy resin (epoxide equivalent weight about 320), 129 parts (1 mole) of 2-ethylhexylamine and 61 parts (1 mole) of monoethanolamine by completely reacting all the epoxy groups. 1900 parts of a bisphenol A-based epoxy resin (epoxide equivalent weight about 475), dissolved in 814 parts of methoxypropanol, are added and allowed to react at 80° C. with the amine until the molar epoxide groups corresponding to the secondary amino groups are consumed. 204 parts (2.0 moles) of dimethylaminopropylamine and 66 parts (2.0 moles) of 91% paraformaldehyde are then added as well as xylene as entraining agent for the azeotropic distillation at 90° to 140° C. When the oxazolidine has formed, the xylene is removed from the reaction medium by distillation and the mixture is diluted with 250 parts of ethylene glycol monobutyl ether. The hydroxyl value of the primary hydroxyl groups is about 19 mg KOH/g, the calculated molecular weight about 2960, and the solids content about 74%.

(B) Production of the Organotin Preparations

The dispersion medium, protonized with acetic acid if appropriate, and the dibutyltin oxide (DBTO) are mixed to form a homogeneous mixture in accordance with the proportions stated in Table 1, and the mixture is ground in a suitable device, preferably in a bead mill or triple-roll mill, to a particle size of about 3 μm. Table 1 is as follows:

TABLE 1

| Preparation | Dispersion Medium | DBTO | Sn (as metal) % by wt. |
|---|---|---|---|
| K1 | 135 parts of (A1) 9 parts of AC*) | 90 parts | 18.3 |
| K2 | 200 parts of (A2) | 80 parts | 19.1 |
| K3 | 75 parts of (A2) 95 parts of (A3) 8 parts of AC*) | 50 parts | 13.4 |

TABLE 1-continued

| Preparation | Dispersion Medium | DBTO | Sn (as metal) % by wt. |
|---|---|---|---|
| K4 | 100 parts of (A4) 10 parts of AC*) | 25 parts | 9.0 |

*)AC: 5N acetic acid (C) Preparation of Cathodically Depositable Electrocoating Paints Catalyzed by the Organotin Preparations and Performance Testing Thereof Preparation of the Binders Used in Table 2

B 1: 220 parts of nonylphenol (1 mole) are heated in a suitable reaction vessel at 75° C. with 130 parts of diethylaminopropylamine (1 mole) and 100 parts of toluene, and the mixture is then treated, with gentle cooling, with 33 parts of 91% paraformaldehyde (1 mole). The temperature is slowly raised until continuous azeotropic distillation ensues. When 21 parts of water of reaction have been separated off, the toluene is distilled off in vacuo and the product is dissolved in 167 parts of diethylene glycol dimethyl ether.

304 parts (1.0 mole) of a toluylene diisocyanate, semi-blocked with 2-ethylhexanol, are added at 30° to 40° C. with cooling to the solution obtained and the temperature is kept at 40° C. for 1.5 hours until an NCO-value of virtually zero is reached.

Subsequently, 475 parts of a bisphenol A-based epoxy resin (epoxide equivalent weight 475) are dissolved in 200 parts of propylene glycol monomethyl ether, 835 parts of the intermediate prepared above are added and the reaction is allowed to proceed at 95° to 100° C. until an epoxide value of virtually zero is reached. The solids content is about 75%.

B 2: 1000 parts of a bisphenol A-based epoxy resin (epoxide equivalent weight about 500), contained in a reaction vessel fitted with a stirrer, thermometer and reflux condenser, are dissolved in 492 parts of ethyl glycol acetate at 60° to 70° C., 0.2 parts of hydroquinone and 144 parts (2 moles) of acrylic acid are added and the temperature is raised to 100°-110° C. The reaction is allowed to proceed at this temperature to an acid value of below 5 mg KOH/g. The reaction product is then treated at 60° to 70° C. with 652 parts (2 moles) of a monoisocyanate obtained from 1 mole of toluylene diisocyanate and 1 mole of diethylethanolamine (70% solution in methyl isobutyl ketone) and the reaction is allowed to proceed to an NCO-value of virtually zero. The solids content is about 75%.

B 3: 500 parts of a bisphenol A-based epoxy resin (epoxide equivalent weight about 500) are dissolved in 214 parts of propylene glycol monomethyl ether and the solution is reacted at 110° C. with 83 parts of a semiester obtained from phthalic anhydride and 2-ethylhexanol in the presence of 0.5 part of triethylamine as catalyst to an acid value of less than 3 mg KOH/g. 120 parts of an oxazolidine containing NH-functions, obtained from aminoethanolamine, 2-ethyl-hexyl acrylate and formaldehyde, and 26 parts of diethylaminopropylamine are then added and the reaction is allowed to proceed at 80° C. to an epoxide value of virtually zero. The mixture is diluted with 200 parts of propylene glycol monomethyl ether and partially neutralized with 97 parts of 3-N formic acid. The solids content of the product is 58.8%. The resin is mixed, in a solids ratio of 80:20, with a transesterification curing agent, prepared as described below. The binder B 3 prepared in this way has a solids content of 64%.

Preparation of the Transesterification Curing Agent 33 parts of 91% paraformaldehyde are added in portions at 70° C. to a mixture of 160 parts of diethyl malonate, 0.85 part of piperidine and 0.54 part of 85% formic acid at such a rate that the exothermic reaction initiated does not cause the temperature to exceed 90° C. The reaction mixture is further stirred at 90° C. until the paraformaldehyde has completely dissolved. The temperature is raised to 140° C. in the course of 2 hours, water commencing to separate. When 140° C. has been reached, 24 parts of water are distilled off using petroleum ether (boiling range 80° to 120° C.) as entraining agent. The entraining agent used is then distilled off in vacuo and the mixture is kept at 120° C. until the specified viscosity and refractive index are reached. The product obtained has a solids content (120° C., 30 minutes) of 97±1%. The Gardner-Holdt viscosity of a sample of 9 g of resin solution and 1 g of ethylglycol is M. The free formaldehyde content is below 1.5% and a determination of the refractive index produces the value of n20/D=1.4560. The compound has an average molecular weight of about 500. The ester functionality is 6 ester equivalents per mole or 1.17 ester equivalents per 100 g of the product.

Pigmented paints are prepared in a known manner in accordance with the data summarized in Table 2, as follows:

TABLE 2

| Ex. | Binder (100 parts of solid resin) | Formic acid (mmoles) | Parts of pigment mixture[1] | Parts of preparation | % by wt. of Sn per 100 parts of binder |
|---|---|---|---|---|---|
| 1 | B 1 | 50 | 55 | 3.8 of K1 | 0.7 |
| 2 | B 1 | 50 | 50 | 4.2 of K2 | 0.8 |
| 3 | B 1 | 50 | 50 | 7.5 of K3 | 1.0 |
| 4 | B 2 | 60 | 35 | 6.7 of K4 | 0.6 |
| 5 | B 2 | 60 | 35 | 7.5 of K3 | 1.0 |
| 6 | B 3 | 50 | 40 | 5.2 of K2 | 1.0 |

[1]Pigment mixture:
2 parts of carbon black
94 parts of titanium dioxide (rutile)
4 parts of basic lead silicate (about 75% by weight of Pb)

The paints, diluted with deionized water to a solids content of 20%, are sedimentation stable for 3 weeks at room temperature. Stir stability (stirring of the paint in an open vessel at room temperature) is satisfactory for all paints after 8 weeks, i.e., no changes in the stoved paint films are discernible.

The paints are electrically deposited on a degreased steel panel, the conditions being chosen such that the film thickness of the stoved films is about 20±2 μm. The crosslinking of the films is carried out at 180° C. for 20 minutes. In no case are any surface defects, such as pinholing or cratering, observed with the "horizontal coating" procedure. In "horizontal coating" a steel panel (about 10×20 cm) is bent at a right angle in the center. The panel is suspended in the coating bath in such a way that the horizontal arm of the L-shaped steel panel is situated about 15 cm below the surface of the paint bath and the vertical arm is pointing upwards. The coating is effected over a coating period of about 4 minutes with the stirrer switched off. At the end of the coating period the panel is allowed to remain in the bath for 2 minutes. It is then withdrawn from the bath, rinsed with water after a further 2 minutes, and stoved. The surface of the paint is assessed for surface defects.

Comparison Examples

For comparison, a paint corresponding to Example 1 was catalyzed by the addition of 0.7% by weight of dibutyltin dilaurate instead of the organotin preparation used according to the invention. The comparison paint shows distinct sedimentation after only 3 days.

In a further comparison, a catalyst-free paint of the above composition was catalyzed using a condensation product from 1 mole of 2-ethylhexanol and 0.5 mole of DBTO. The paint was sedimentation stable, but in the "horizontal coating" procedure exhibited film defects in the form of pinholing.

As will be apparent to one skilled in the art, various modifications can be made within the scope of the aforesaid description. Such modifications being within the ability of one skilled in the art form a part of the present invention and are embraced by the appended claims.

It is claimed:

1. Organotin compositions comprising dibutyltin oxide present in a particle size of from 0.1 to 5 μm and a dispersion medium comprising
    (a) 60 to 100% by weight of at least one substituted oxazolidine compound which is the reaction product of a hydroxyalkylamino compound and formaldehyde which contains at least one oxazolidine structural unit and has a hydroxyl value, based on primary hydroxyl groups, of up to 50 mg KOH/g and a (calculated) molecular weight of 500 to 4000,
    (b) 0 to 40% by weight of at least one water-tolerant solvent which is compatible with component (a), is non-reactive toward dibutyltin oxide and has a boiling point between 150° and 250° C., and
    (c) 0 to 40% by weight of at least one water-tolerant solvent having a boiling point between 100 and up to 150° C.,
the percentages of components (a), (b) and (c) totalling 100 and the organotin compositions having a dibutyltin oxide content, based on the tin content, of 5 to 30% by weight.

2. The organotin composition of claim 1 wherein said substituted oxazolidine compound is partially or fully protonized.

3. The organotin composition of claim 2 wherein said component (b) includes up to 20% by weight based on the amount of component (b) of surfactant.

4. The organotin composition of claim 3 wherein the dibutyltin oxide content based on tin content is from 12 to 25% by weight.

5. A process for the production of the organotin composition of any one of claims 1–4 wherein said dibutyltin oxide is mechanically dispersed in said dispersing medium.

6. A catalyzed cationic paint comprising a paint binder and 0.1 to 3.0% by weight of tin, calculated on the binder solids, contributed by an organotin composition of any one of claims 1–4.

7. The catalyzed cationic paint of claim 6 wherein the tin content is from 1.0 to 2.0% by weight of tin, calculated on the binder solids.

* * * * *